US00PP15048P3

(12) United States Plant Patent
Goemans

(10) Patent No.: US PP15,048 P2
(45) Date of Patent: Jul. 27, 2004

(54) ALSTROEMERIA PLANT NAMED 'CHRISTINA'

(50) Latin Name: *Alstroemeria hybrid*
Varietal Denomination: Christina

(75) Inventor: Robert Adrian Goemans, Chichester (GB)

(73) Assignee: Wülfinghoff Alstroemeria B.V. (NL)

( * ) Notice: Subject to any disclaimer, the term of this patent is extended or adjusted under 35 U.S.C. 154(b) by 72 days.

(21) Appl. No.: 10/097,253

(22) Filed: Mar. 15, 2002

(65) Prior Publication Data

US 2003/0177558 P1 Sep. 18, 2003

(51) Int. Cl.[7] ..... A01H 5/00

(52) U.S. Cl. ..... Plt./309

(58) Field of Search ..... Plt./309

*Primary Examiner*—Bruce R. Campell
*Assistant Examiner*—Louanne Krawczewicz Myers
(74) *Attorney, Agent, or Firm*—Foley & Lardner

(57) ABSTRACT

A new and distinct Alstroemeria plant named 'Christina' characterized by growth height of 10–30 cm under greenhouse conditions; suitable for pots larger than 7 cm; growth height of 10–30 cm; bushy-dwarf growth habit; inner tepals, RHS 4D at the apex, RHS 9A at the center, RHS 54C at the base, with stripes RHS 187A (upper surface); outer tepals RHS 4D, with a smudge of 54C at the center (upper surface); and 4–6 weeks inflorescence longevity.

1 Drawing Sheet

Latin name of the genus and species of the plant named: Alstroemeria hybrid.
Variety denomination: 'Christina'.

BACKGROUND OF THE NEW VARIETY

The present invention comprises a new and distinct cultivar of Alstroemeria plant, hereinafter referred to by the cultivar name 'Christina'.

'Christina' originated from a hybridization made in a controlled breeding program in Chichester in Sussex, United Kingdom by the inventor Robert Adrian Goemans. The male parent is an unnamed dwarf Butterfly type cultivar (unpatented). The female parent of 'Christina' is an unnamed, unpatented, *Alstroemeria aurea* selection.

'Christina' was discovered and selected as one flowering plant within the progeny of the stated parentage by Robert Adrian Goemans in 1997 in a controlled environment in Chichester, United Kingdom. The first act of asexual reproduction of 'Christina' was accomplished when vegetative cuttings were taken from the initial selection in May, 1999 in a controlled environment in Chichester, United Kingdom. Horticultural examination of selected plants initiated in 1999 has demonstrated that the combination of characteristics as herein disclosed for 'Christina' are firmly fixed and retained through successive generations of asexual reproduction.

BRIEF SUMMARY OF THE INVENTION

The following traits have been repeatedly observed and are determined to be basic characteristics of which in combination distinguish this Alstroemeria as a new and distinct cultivar:

1. Suitable for pots larger than 7 cm.
2. growth height 10–30 cm under greenhouse conditions;
3. bushy-dwarf growth habit;

4. inner tepals, RHS 4D at the apex, RHS 9A at the center, RHS 54C at the base, with stripes RHS 187A (upper surface); outer tepals RHS 4D, with a smudge of 54C at the center (upper surface); and
5. 4–6 weeks inflorescence longevity.

There are no commercial cultivars known to the inventor, similar in comparison to 'Christina'. In comparison to 'Christina', the female parental cultivar has blue flowers and is small in size, having a dwarf growth habit; and the male parental cultivar has yellow flowers and is tall in size.

'Christina' has not been observed under all possible environmental conditions. The phenotype may vary significantly with variations in environment such as temperature, light intensity and day length, without any change in genotype. The following observations, measurements and comparisons describe plants grown in Chichester, Sussex, United Kingdom under greenhouse conditions which approximate those generally used in commercial practice.

BRIEF DESCRIPTION OF THE DRAWINGS

The accompanying photographic drawing shows a typical plant of the new variety with colors as accurate as is possible with this type of drawing.

The photographic drawing shows the flowers and foliage of 'Christina'.

DETAILED BOTANICAL DESCRIPTION

In the following description, color references are made to The Royal Horticultural Society Colour Chart (R.H.S.). The color values were determined in the afternoon of Sep. 16, 2000 under normal daylight conditions in Wateringen, The Netherlands. The plants described are nine months of age and grown in 15 cm pots. The plants were asexually propagated by rooted tissue cultured rhizomes.

Classification:

*Botanical.*—Alstroemeria hybrid.

*Commercial.*—Alstroemeria cv. Christina.

Plant:

*Form.*—Pot Plant.

*Height.*—10–30 cm (Dutch greenhouse conditions).

*Diameter.*—18 cm.

*Growth.*—Bushy-dwarf growth habit.

*Time it takes to produce a flowering plant.*—From planting of rooted tissue cultured rhizomes to flowering is 6 to 9 months, depending on cultural conditions.

*Number of lateral branches.*—38 per plant.

*Stem.*—Size: 14 cm in length, 4 mm in diameter. Texture: Firm/fleshy. Color: RHS yellow-green group 149 C. Length of internode: 5 mm.

Foliage:

*Quantity.*—5–10 leaves on each centimeter of stem, depending on growth stage.

*Size of leaf.*—Length: 70–90 mm; width: 30–35 mm.

*Shape of leaf.*—Oblong-ovate; cuspidate apex; cuneate base; dentate margin.

*Texture of leaf.*—Smooth and firm.

*Color.*—Upper side is dark green, RHS 137 A to RHS 137 B. Underside is light-green, RHS 137 C.

*Petioles.*—Length: 21 mm; width: 4 mm; green in color, RHS 143 C.

*Rhizomes.*—Color: White RHS 158 A to RHS 158 D. Size: length 10–50 mm; diameter 6–15 mm, depending on age.

Inflorescence:

*Number of flowers per cyme.*—1–2.

*Number of flowers per umbel.*—2–3.

*Number of open flowers per plant.*—Typically 12–15 per 15 cm pot.

*Lasting quality of the bloom.*—4–6 weeks on the plant.

*Flowering season.*—May–September under outdoor conditions.

*Fragrance.*—None.

Bud:

*Form.*—Tubular pointed.

*Diameter.*—10–20 mm.

*Length.*—15–25 mm.

*Peduncle.*—20–25 mm, medium-green RHS 145 A.

*Color.*—Red, RHS 46 A to RHS 46 B.

Flower:

*Size.*—Medium, length: 40–60 mm; width: 40–60 mm.

*Shape.*—Broad obovate.

*Tepals.*—Outer tepals: 3. Size: length: 55 mm, width 31 mm. Upper Surface Color: RHS 4D, with a smudge of RHS 54C at the center. Under Surface Color: RHS 4D, with a central stripe of RHS 54C. Shape: broad obovate. Apex: cuspidate. Base: cuneate. Margin: serrate. Texture: silky. Inner tepals: 3. Size: length 60 mm, width 18 mm. Upper Surface Color: RHS 4D at the apex, RHS 9A at the center, RHS 54C at the base with stripes RHS 187A. Lower Surface Color: RHS 4D at the apex, RHS 8A at the center, RHS 54C at the base. Shape: spatulate. Apex: cuspidate. Base: cuneate. Margin: dentate. Texture: silky.

*Peduncle.*—Length: 40–50 mm. Color: Medium-green, RHS 145 A.

Reproductive organs:

*Stamens.*—6.

*Pollen.*—Plentiful, yellow RHS 9 A.

*Anthers.*—Yellow, RHS 13 A.

*Filaments.*—Red, RHS 50 A to RHS 50 B.

*Pistils.*—1, red-pink, RHS 50 B to RHS 50 C.

*Stigma.*—Pink-white, RHS 56 A to RHS 56 C.

*Seeds.*—None.

Disease/pest resistance/susceptibility: No known information.

I claim:

1. A new and distinct Alstroemeria plant named 'Christina', as described and illustrated herein.

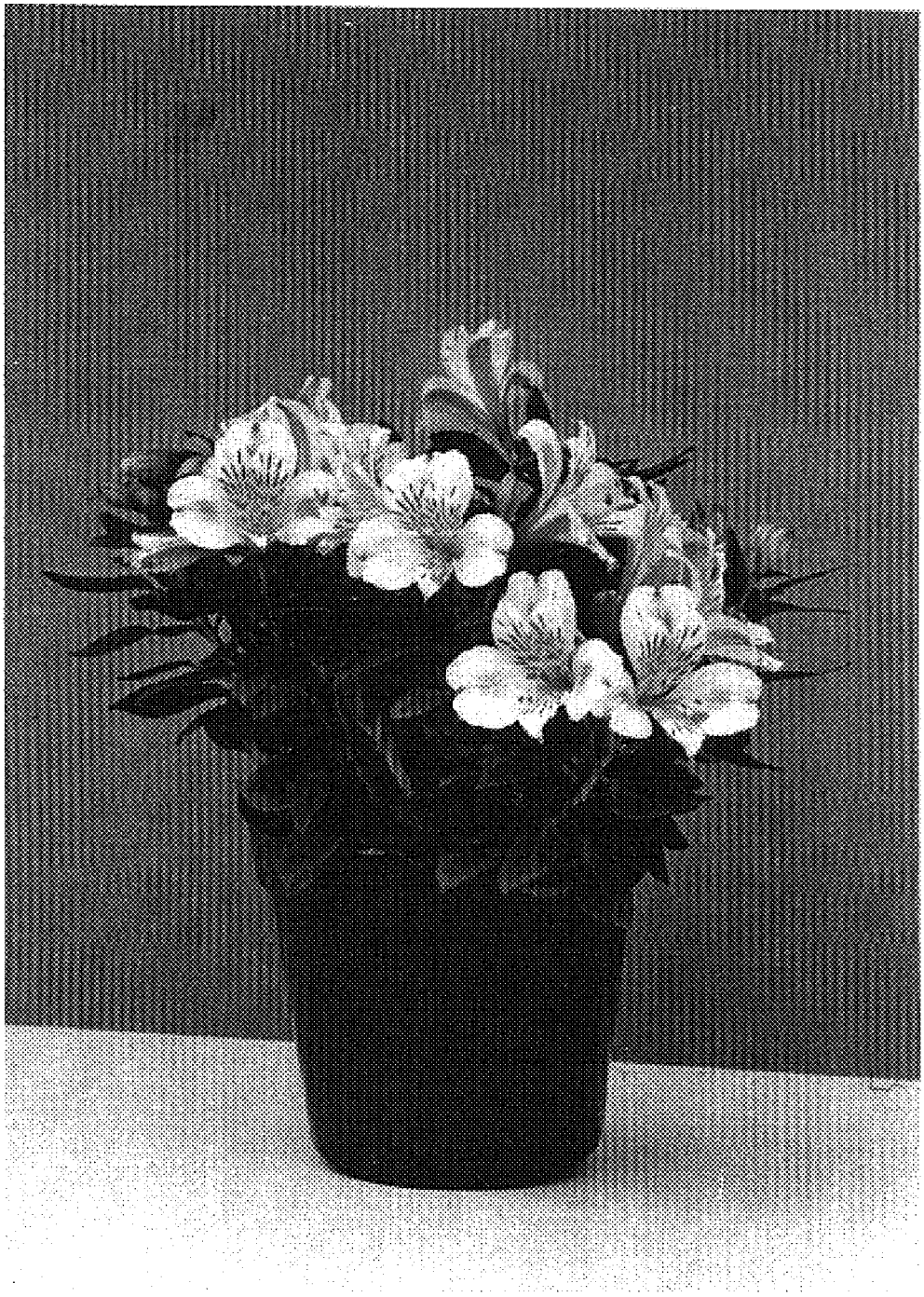

* * * * *